United States Patent [19]

Andriola et al.

[11] Patent Number: 4,666,441
[45] Date of Patent: May 19, 1987

[54] MULTICOMPARTMENTALIZED TRANSDERMAL PATCHES

[75] Inventors: Robert Andriola, Putnam Valley; Donald J. Moore, Pomona, both of N.Y.; Henning Asche, Bettingen, Switzerland

[73] Assignee: Ciba-Geigy Corporation, Ardsley, N.Y.

[21] Appl. No.: 810,102

[22] Filed: Dec. 17, 1985

[51] Int. Cl.⁴ .............................................. A61K 9/00
[52] U.S. Cl. .................................... 604/897; 604/304
[58] Field of Search ............................. 604/303–308, 604/890–892, 897; 424/28; 128/156

[56] References Cited

U.S. PATENT DOCUMENTS

| | | |
|---|---|---|
| 2,807,262 | 9/1957 | Lew ...................................... 604/307 |
| 3,598,122 | 8/1971 | Zaffaroni . |
| 3,598,123 | 8/1971 | Zaffaroni . |
| 3,731,683 | 5/1973 | Zaffaroni . |
| 3,734,097 | 5/1973 | Zaffaroni . |
| 3,742,951 | 7/1973 | Zaffaroni . |
| 3,797,494 | 3/1974 | Zaffaroni . |
| 3,996,934 | 12/1976 | Zaffaroni . |
| 4,336,243 | 6/1982 | Sanvordeker et al. ............. 604/897 |
| 4,379,454 | 4/1983 | Campbell et al. ................... 604/897 |
| 4,460,372 | 7/1984 | Campbell et al. ................... 604/897 |
| 4,486,193 | 12/1984 | Shaw et al. .......................... 604/890 |
| 4,588,580 | 5/1986 | Gale et al. ........................... 604/897 |

OTHER PUBLICATIONS

Strategic Technologies (1985), pp. 92–98.

Primary Examiner—C. Fred Rosenbaum
Assistant Examiner—Jerome R. Smith, Jr.
Attorney, Agent, or Firm—Irving M. Fishman

[57] ABSTRACT

A dermal or transdermal patch comprising (1) a backing layer which is non-permeable with respect to a drug formulation to be contained within the patch, (2) a membranous layer, which is permeable to the drug, having a first surface partially in contact with said backing layer so as to define multiple compartments, (3) at least one drug or drug formulation contained within said compartments, (4) an adhesive layer on a second surface of said membranes layer, and (5) a peelable protective cover layer on said adhesive layer.

19 Claims, 20 Drawing Figures

MULTICOMPARTMENTALIZED TRANSDERMAL PATCHES

In recent years, patches for delivering drugs for systemic absorption through the skin (transdermal) have become increasingly important. As experience with this means of drug delivery has grown, it has been recognized that a greater and greater number of systemically active drugs can be administered via the transdermal route. A good deal of the importance of this means of administration resides in the fact that drugs can be delivered to the bloodstream without traversing the gastro-intestinal tract and avoiding a first pass through the hepatic system prior to reaching the target site. At the same time, transdermal medication can obtain these benefits without requiring a professional to administer the drug.

Since self-administration is generally involved, patient compliance with application instructions and the abiity of the product to remain unchanged from the time of manufacture take on greater importance than otherwise. Increasing pysical changes in the distribution of the active ingredients and vehicle over the product shelf-life (especially as with respect to coverage of the patch surface area in a uniform manner), require a greater degree of care and attention by the patient or other person administering the patch. This is a particular problem with those patches having a permeable membrane through which an active agent moves from an enclosed space within the patch to the skin.

In such a system (one of the types described in U.S. Pat. Nos. 3,996,934; 3,797,494; 3,742,951; and 3,598,122) the drug or drug formulation is generally contained within a "sack" formed from a non-porous backing material and a porous membranous layer. On the "outer" surface of the membranous layer is a coating of an adhesive, which is further covered by an occlusive protecting layer. The protecting layer is removed by the patient or person administering the patch immediately prior to applying the patch to the skin.

Frequently, the dermal and transdermal patches described above suffer from the defect that the drug or drug formulation contained within the "sack" sinks or migrates to the bottom, i.e. when the patch is stored in an "on edge" orientation—a common storage position by those in the chain of distribution of the product as well as by patients. This is particularly evident when patches having a drug reservoir (one sided) surface area of about 30 cm² or larger. Hence, when the patch is to be applied, the user must insure that the drug formulation is evenly spread over the entire available surface area of the "sack" interior. Unfortunately, not all patients or those applying the patch can be relied upon to recognize the defect and properly correct it.

Furthermore, unless the defect is properly remedied, the rate of transference of the drug from the patch to the skin will be significantly altered from that intended. Some portions of the skin will be undermedicated. When the desired delivery rate exceeds the skin's absorption rate, a significant portion of the drug may be wasted from the acumulation of migrated drug. When the intended delivery rate is less than the skin absorption rate, undermedicated areas will receive less than the intended dose. The patient receives improper treatment.

Another problem involving patches having active drug formulatons which are semi solid or liquid, or become so at body temperature, is similar drug formulation migration while the patch is being worn, especially with larger sizes designed for application to the trunk and other body parts which will be in a vertical position for an extended period. Here it is very unlikely that the patient will even be aware that a problem exists, let alone correct it.

It is an object of this invention to provide dermal and transdermal patches of the "sack" type which overcome these defects.

Another object of this invention is to provide dermal and transdermal patches in which patient interaction with the patch is reduced to removing the protective layer and applying the patch, without concern for any drug formulation migration therein.

A further object of the invention is to provide dermal and transdermal patches which can be stored in any orientation without concern.

A still further object of the invention is to allow the use of drug vehicles in "sack type" transdermal patches which have hitherto been unsuitable therefor.

Suprisingly, these objects, and others, have been achieved by compartmentalizing the "sack" area containing the drug or formulation into a number of smaller, distinct "sacks" or compartments.

The patches of the invention will be better understood with reference to the drawings in which like referenced numerals indicate like parts. Of course these drawings are exemplary only and do not limit the scope of the invention to the embodiments shown therein.

DETAILED DESCRIPTION OF THE INVENTION

The instant invention is an improved dermal or transdermal patch having a drug or drug formulation contained within a drug compartment area adapted to be applied directly to the skin of a patient to be treated with the drug. The improvement resides primarily in splitting the drug reservoir 2 in FIGS. 1-4 into multiple compartments 8, as seen in FIGS. 5-17.

Figure 1:
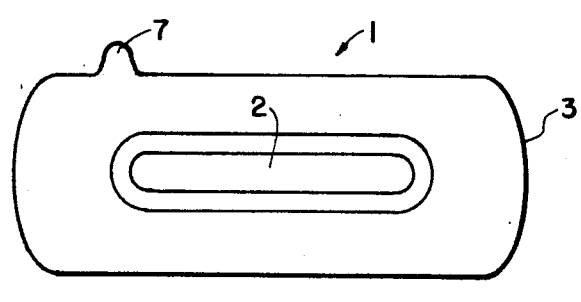
FIGS. 1 and 3 are top views of two prior art patch embodiments.
Figure 2:
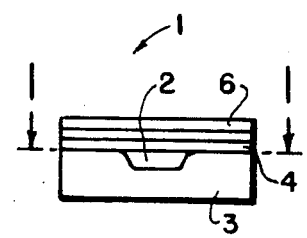
FIGS. 2 and 4 are cross-sections of a typical prior art patches.
Figure 3:
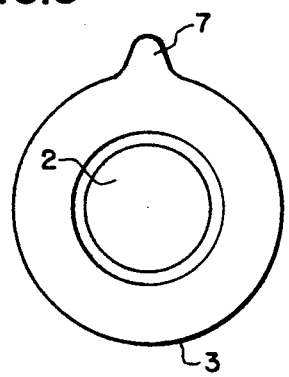
Figure 4:
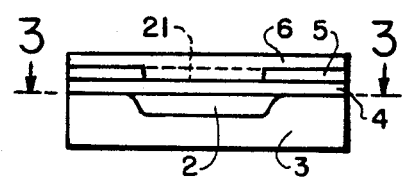
Figure 5:
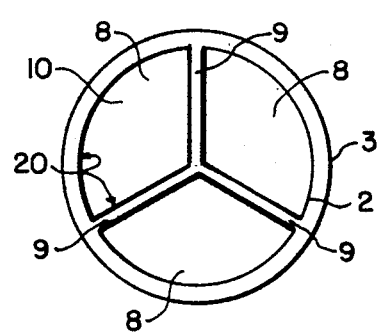
FIGS. 5-8 are top views of 4 embodiments of the invention.
Figure 6:
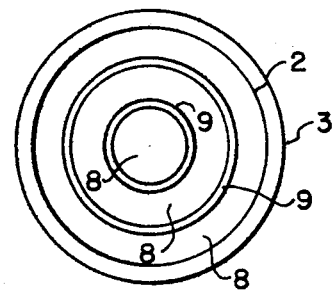
Figure 7:
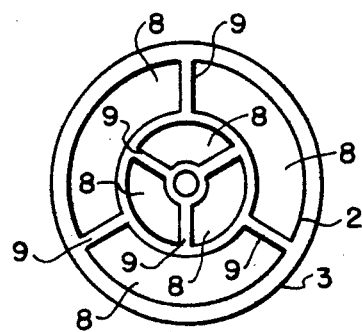

With reference to FIGS. 1-4, the previously known patches 1 of this type were comprised of an occlusive protective backing layer 3, a permeable porous membrane 4 thereon forming therewith a total reservoir area 2, an adhesive layer 5 on the surface of porous membrane 4 (which adhesive layer is remote from the interior of reservoir 2 and backing layer 3), and an occlusive, removable layer 6 on adhesive 5. The adhesive layer 5 may be over the entire surface of reservoir 2, as shown in FIG. 2 or define an adhesive free area 21 (see FIG. 4) over the reservoir. As readily seen from FIGS. 5–16, the invention is a similar patch except that the reservoir 2 has been broken up into a number of distinct compartments 8 by seals 9. Tab 7 is not shown in FIGS. 5, 6, and 7.

The size of each compartment 8 should not exceed 30 cm², preferably 26.7 cm², more preferably 20 cm², most preferably 13.3 cm². The maximum distance between the center of gravity 10 (see FIG. 5) of a compartment and any border 20 of that compartment should not exceed 2.70 cm, preferably 2.55 cm, more preferably 2.23 cm, most preferably 1.78 cm, and the perimeter of the compartment should not exceed 4.04 times the square root of the compartment area. While there is no concern over the compartment shape, the latter two limitations above do not apply if compartments are bounded by (a) arcs of concentric circles (see FIG. 6) or (b) are polygonal or of indiscriminate in shape and can be inscribed within a rectangle having a smaller perimeter.

Preferred patch shapes, exclusive of tab, 7 (used as a point from which the user can remove the protection layer), are: oval, eliptical, circular, and rectangular or rectangular-like but having 2 arcuate ends opposite one another (see FIG. 8), although other shapes can also be used. Of these, circular and rectangular-like but having 2 substantially semi-circular opposing ends are more preferred and circular is most preferable.

The boundaries between adjacent compartments (the inter compartment seals 9, 12 and 13), can be of any orientation; however, straight lines extending radially outward from the center of gravity of the entire patch or from the center of a circle, a portion of which forms more than a tangential portion of the outer perimeter of the medication containing surface area of the patch are preferred. Also preferred are vertical or horizontal borders, especially a crosshatch pattern. Of course, combinations of various types are also suitable, especially in the case wherein concentric circles form some of boundaries of some of the compartments.

An additional advantage of compartmentalization of the patch is the ability to vary the drug vehicle to an extent heretofore impossible to accomplish. More fluid vehicles than the currently used viscous ointments can now be effectively utilized. This means that the present invention allows one to flexibly utilize drug formulations giving a greater range of release rates and more precisely control drug delivery to the skin. In effect, the instant invention allows one to utilize any vehicle which (1) will release the drug to the porous membraneous layer 4 and (2) does not adversely interact with membranous layer 4 or backing layer 3.

A still further advantage of this invention is the ability to regulate drug delivery by the simple means of having (1) different concentrations of drug in different compartments, (2) different vehicles having different drug release rates in different compartments, (3) additives such as flux enhancers in some, but not all compartments, and/or (4) having different materials, having different drug transference rates, forming the membranous layer of different compartments. Also, different adhesive coatings 5 on the membranous layer 4 over different compartments 8 may be utilized to alter drug delivery. Via any of these means the drug delivery rate of the overall patch can be more precisely regulated so as to yield the desired controlled, reliable, reproduceable results.

Of course, one can also load different compartments 8 with different drugs that are desirable to be administered simultaneously, stepwise, or any other precisely regulated manner. Such a system virtually eliminates problems of patient compliance as only a single patch need be applied. This system also permits the coadministration or precisely tailored administration of two or more drugs, which are incompatible with each other or the vehicles used, in a single patch.

Figure 19:
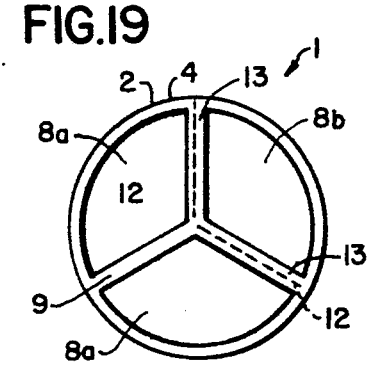
FIG. 19 is a top view of a "back-up reserve" or "superloaded" compartment embodiment of the invention.
Figure 20:
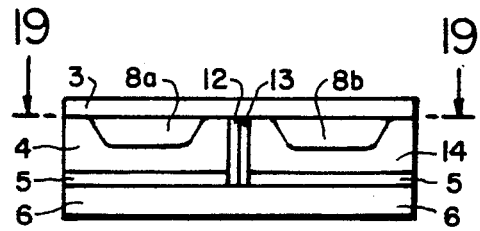
FIG. 20 is a cross section of FIG. 19 along line 20—20.

The new patches can also be used to create a new means of sustained release administration of a drug. For example, in a three compartment patch, as in FIGS. 19 and 20, if two components have a first concentration of a drug and the third compartment has a much higher concentration, then via a burstable non-permeable (to drug) membrane 13 (which is burst just prior to or during application of the patch), and optionally a permeable non-bursting membrane 13, forming the seal between the low concentration and high concentration compartments, with a non-pourous membrane 14 covering the high concentration compartment instead of or in addition to the porous membranous layer 4, the high concentration compartment acts as a high load reserve to maintain the concentration of drug in the low concentration compartment at an appropriate level for a much longer period. When the non porous membrane is not used, the difference in transference rates and absorption rates due to the different concentrations can be exploited to obtain an initial loading dose with subsequent decrease to typical maintenance levels.

More specifically, with the application of certain drugs, particularly nitroglycerine, it is advantageous to administer the drug at one rate for a set period and at a lower rate for an additional period.

Such a scheme has not been practical using a single reservoir compartment patch. However with multicompartment patches having different concentrations of drug in different compartments such a drug dose regimen can easily be obtained.

If a patch having 25% of theoretical nitroglycerine loading in each of two compartments of equal size and a third compartment of the same size having 100% of theoretical nitroglycerine loading is administered, for 16 hours the patient is receiving a loading dose. Over this time the low dose compartments have been essentially depleted, yet the high dose compartment still has a substantial amount of drug remaining; an amount sufficient to deliver a therapeutic level of medication for the remainder of the day.

This method of administration is particularly convenient when oral loading doses which are maintained at those levels are hampered by undesirable side effects, yet single, once daily dosing is of importance (particularly so with the elderly or senile patient).

Another potential of the patch with a burstable membrane between compartments is in the case wherein a particular formulation must be applied within a short time of mixing the ingredients. In these cases, the patches are loaded with the different ingredients in different compartments. The seal between the compartments is ruptured and the contents worked together by the user. The patch is then applied.

Figure 18:
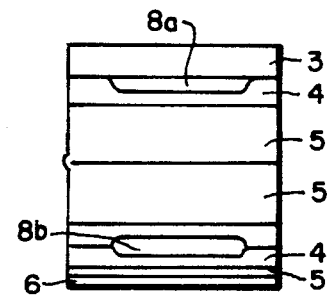
FIG. 18 is the embodiment of FIG. 17 after folding.
Figure 17:
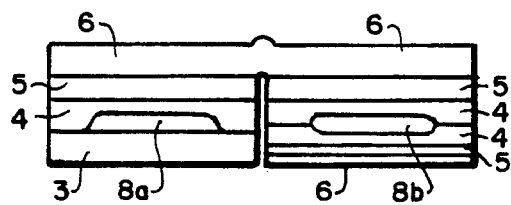
FIG. 17 is a cross section of a "fold-over" embodiment of the invention before use.

An alternative embodiment of the patch having different ingredients in different compartments, which are to be mixed immediately prior to or at the time of applying the patch is the case wherein the patch as seen in FIGS. 17 and 18, after removal of an occlusive removable layer 6, folds over on itself, joining two different compartments together so that their contents may mix together. In this position the patch resembles those previously described except that in cross-section it appears as though the center of Reservoir 2 has an additional permeable double membrane and adhesive layers (essentially parallel to the backing layer) passing therethrough.

The patches of the instant invention are prepared in typically known manners. Advantageously the boundaries between compartments, when they are not burstable, are heat sealed. However, other methods will be obvious to those of ordinary skill.

The patch of the instant invention can be used to deliver any drug to the skin in a controlled manner. The only limitation on the drugs which are useful in the present invention are that they are either (1) transdermally absorbed (with or without a flux enhancer) at a level sufficient to elicit a therapeutic systemic response or (2) elicit a therapeutic topical response. Of course, they must be capable of traversing the porous membrane and, in appropriate circumstances, the adhesive employed to fix the patch to the skin.

In practicing this invention one can employ any systemically active drug which will be absorbed by the body surface to which the bandage is applied, consistent with their known dosages and uses. Of course, the amount of drug necessary to obtain the desired therapeutic effect will vary depending on the particular drug used. Suitable systemic drugs include, without limitation, Anti-microbial Agents such as penicillin, tetracycline, oxytetracycline, chlortetracycline, chloramphenicol, and sulfonamides; Sedatives and Hypnotics such as pentabarbital sodium, phenobarbital, secobarbital sodium, codeine, (a-bromoisovaleryl)urea, carbromal, and sodium phenobarbital, Psychis Energizers such a 3-(2-aminopropyl) indole acetate and 3-(2-aminobutyl) indole acetate; Tranquilizers such as reserpine, chlorpromazine hydrochloride, and thiopropazate hydrochloride; Hormones such as adrenocorticosteroids, for example 6α-methylprednisolone; androgenic steroids, for example, methyltestosterone, and fluoxymesterone; estrogenic steroids, for example estrone, 17β-estradiol and ethinyl estradiol; progesterone, and norethindrone; and thyroxine; Antipyretics such as aspirin, salicylamide, and sodium salicylate; morphine and other narcotic analgesics; Anti-diabetics, e.g., insulin; Cardiovascular Agents, e.g. nitroglycerin, and cardiac glycosides such as digitoxin, digoxin, ouabain; Anti-spasmodics such as atropine, methscopolamine bromide, methscopolamine bromide with phenobarbital; Anti-malarials such as the 4-aminoquinolines, 9-amino-quinolines, and pyrimethamine; and Nutritional Agents such as vitamins, essential amino acids, and essential fats.

Additionally, in practicing this invention one can employ a wide variety of topically active drugs consistent with their known dosages and uses. Suitable drugs include, without limitation: Antiperspirants, e.g., aluminum chloride; Deodorants, e.g., hexachlorophene, methylbenzethonium chloride; Astringents, e.g., tannic acid; Irritants, e.g., methyl salicylate, camphor, cantharid, 1; Keratolytics, e.g., benzoic acid, salicylic acid, resorcinol, iodochlorhydroxyquin; Antifungal Agents, such as tolnaftate, griseofulvin, nystatin and amphotericin; Anti-inflammatory Agents, such as corticosteroids, e.g., hydrocortisone, hydrocortisone acetate, prednisolone, methylprednisolone, triamoinolone acetonide, fludrocortisone, flurandrenolone, flumethasone, dexamethasone sodium phosphate, bethamethasone, desamethasone sodium phosphate, bethamethasone valerate, fluocinolone acetonide; fluorometholone; and pramoxine HC1; Anti-neoplastic Agents, e.g. methotrexate, and Antibacterial Agents, such a bacitracin, neomycin, erythromycin, tetracycline HC1, chlortetracycline HC1, chloramphenicol, oxytetracycline, polymyxin B, nitrofuraxone, mafenide (α-amino-p-toluenesulfonamide), hexachlorophene, benzalkonium chloride, cetalkonium chloride, methylbenzethonium chloride, and neomycin sulfate.

It will be appreciated, with regard to the aforesaid list of drugs the characterization of the drug as eithere "systemically or topically" active is done for purposes of convenience only. Further, a given drug can be both systemically and topically active depending upon its manner of use.

In addition to the aforementioned drugs, simple pharmacologically acceptable derivatives of the drugs, such as ethers, esters, amides, acetals, salts, etc., or formulations of these drugs, having the desired polymeric permeability or transport or transport properties can be prepared and used in practicing the invention. Drugs mentioned above can be used along or in combination with others and each other. Of course, the derivatives should be such as to convert to the active drugs within the body through the action of body enzyme assisted transformation, pH, etc.

The above drugs and other drugs can be present in the reservoir along or in combination form with pharmaceutical carriers. The pharmaceutical carriers acceptable for the purpose of this invention are the art known carriers that do not adversely affect the drug, the host, or the material comprising the drug delivery device. Suitable pharmaceutical carriers include sterile water; saline, dextrose; dextrose in water or saline, condensation products of castor oil and ethylene oxide combiniang about 30 to 35 moles of ethylene oxide per mole of castor oil; liqud glyceryl triester of a lower molecular weight fatty acid; lower alkanols, oils such as corn oil, peanut oil, sesame oil and the like, hydrocarbons such as mineral oils and silicones, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrrolidone); and the like, alone, or with suitable dispersing agents such as lecithin; polyoxyethylene stearate; and the like. The carrier may also contain adjuvants such as preserving, stabilizing, wetting, emulsifying agents, and the like.

The drug can also be mixed in the reservoir with a transporting agent, that is, a material that aids or assists the drug delivery device to achieve the administration of a drug to a drug receptor, for example, by enhancing penetration through the skin. The transporting aids suitable for the purpose of the invention are the therapeutically acceptable transporting aids that do not adversely affect the host, the drug, or alter or adversely affect the materials forming the drug delivery device. The transporting aids can be used alone or they can be admixed with acceptable carriers and the like. Exemplary of transporting aids include monovalent, saturated and unsaturated aliphatic cycloaliphatic and aromatic alcohols having 4 to 12 carbon atoms, such as hexanol, cyclohexane and the like; aliphatic cycloaliphatic and aromatic hydrocarbons having from 5 to 12 carbon atoms such as hexane, cyclohexane, isopropylbenzene and the like; cycloaliphatic and aromatic aldehydes and ketones having from 4 to 10 carbon atoms such as cyclohexanone; acetamide; N,N-di(lower) alkyl acetamides such as N,N-diethyl acetamide, N,N-dimethyl acetamide, N-(2-hydroxyethyl) acetamide, and the like; and other transporting agents such as aliphatic, cycloaliphatic and aromatic esters; N,N-di(lower) alkyl sulfoxides; essential oils; halogenated or nitrated aliphatic, cycloaliphatic and aromatic hydrocarbons; salicylates; polyalkylene glycol silicates; mixtures thereof; and the like.

The amount of active agent to be incorporated in the patch to obtain the desired therapeutic effect will vary depending upon the desired dosage, the permeability of the rate controlling materials of the patch which are employed to the particular agent to be used, and the length of time the patch is to remain on the skin or body mucosa. Since this invention is designed to control drug administration for an extended period of time, such as 1 day or more, there is no critical upper limit on the amount of agent incorporated therein. The lower limit is determined by the fact that sufficient amounts of the agent must remain in the bandage to maintain the desired dosage. In order to achieve a therapeutic effect in a human adult, the daily release dosage of atropine should be in the range of between 200 and 600 micrograms per day. Thus, for example, using atropine and with a patch intended to remain in place for 1 week having a release rate of 500 micrograms of atropine per day, at least 3.5 mg of atropine would be incorporated. Of course, other devices for use for different time periods such as week or month are also readily made by the invention.

Nitroglycerine and arecoline are especially suited for use in the instant invention.

Concentrations of the drugs in the compartments are virtually unlimited since delivery rate is controlled by the porous membrane and adhesive layer. However, the concentration must be at least great enough so that the drug will leave the vehicle once the protective layer is removed. Should the amount of drug/unit area/unit time be insufficient to render an appropriate dose of the drug, a larger patch may be employed. However, it is more advantageous to utilize concentrations of drug sufficiently high so that patch size is kept down. Also advantageous are saturated systems. Most advantageous are systems capable of delivering the drug in a therapeutically useful degree in an area reasonably related to the application site in view of medical, aesthetic, and patient convenience considerations. These limitations are well known to product designers in the art.

The porous membranous materials of this invention, which may or may not be rate controlling as desired, are known in the art and can be visualized as a plurality of sponge-like fused polymer particles which provide a supporting structure having therethrough a dispersion of microscopic sized interconnecting voids or pores. The rate controlling structures formed from the materials can be isotropic, wherein the structure is homogenous throughout the cross-section of the matrix or membrane material, or anisotropic wherein the structure is non-homogenous. These structures are commercially available and can be made by a multitude of different methods, e.g., etched nuclear track, and materials employed, e.g., polyelectrolyte, ion exchange polymers, as described in R. E. Kesting, Synthetic Polymer Membranes, McGraw Hill, Chapters 4 and 5, 1971; J. D. Ferry, Ultrafiltration Membranes, Chemical Review, Vol. 18, Page 373, 1934. Materials possessing from 5 percent to 95 percent voids and having an effective pore size of from about 10 angstroms to about 100 microns are particularly suitably employed in the practice of this invention. Materials with pore sizes significantly below 50 angstroms can be considered to be molecular diffusion type membranes and matrices. In order to obtain the most advantageous results, the materials should be formed into structures with the desired morphology in accordance with methods known to those skilled in the art to achieve the desired release rate of drug. Additionally, the material Must have the appropriate chemical resistance to the drug used and be non-toxic when used as an element of the patch of the invention.

Materials useful in forming the porous rate controlling materials used in this invention include, but are not limited to the following.

Polycarbonates, i.e., linear polyesters of carbonic acids in whih carbonate groups recur in the polymer chain, by phosgenation of a dihydroxy aromatic such as bisphenol A. Such material are sold under the trade designation Lexan by the General Electric Company.

Polyvinylchlorides; one such material is sold under the trade designation Geon 121 by B. G. Goodrich Chemical Company.

Polyamides such as polyhexamethylene adipamide and other such polyamides popularly known as "nylon". One particularly advantageous material is that sold under the trade name "NOMEX" by E. I. DuPont de Nemours & Co.

Modacrylic copolymers, such as that sold under the trade designation DYNEL are formed of polyvinylchloride (60 percent) and acrylonitrile (40 percent), styrene-acrylic acid copolymers, and the like.

Polysulfones such as those of the type characterized by diphenylene sulfone groups in the linear chain thereof are useful. Such materials are available from Union Carbide Corporation under the trade designation P-1700.

Halogenated polymers such as polyvinylidene fluoride sold under the trade designation Kynar by Pennsalt Chemical Corporation, polyvinylfluoride sold under the trade name Tedlar by E. I. DuPont de Nemours & Co., and the polyfluorohalocarbon sold under the trade name Aclar by Allied Chemical Corporation.

Polychlorethers such as that sold under the trade name Penton by Hercules Incorporated, and other such thermoplastic polyethers.

Acetal polymers such as the polyformaldehyde sold under the trade name Delrin by E. I. DuPont de Nemours & Co., and the like.

Acrylic resins such as polyacrylonitrile polymethyl methacrylate, poly n-butyl methacrylate and the like.

Other polymers such as polyurethanes, polyimides, polybenzimidazoles, polyvinyl acetate, aromatic and aliphatic, polyethers, cellulose esters, e.g., cellulose triacetate; cellulose; colledion (cellulose nitrate with 11% nitrogen); epoxy resins; olefins, e.g.; polyethylene polypropylene; porous rubber; cross linked poly (ethylene oxide); cross-linked polyvinylpyrrolidone; cross-linked poly(vinyl alcohol); polyelectrolyte structures formed of two ionically associated polymers of the type as set forth in U.S. Pat. Nos. 3,549,016 and 3,546,141; derivatives of polystyrene such as poly(sodium styrenesulfonate) and polyvinylbenzyltrimethyl-ammonium chloride); poly(hydroxyethylmethacrylate); poly(isobutylvinyl ether), and the like, may also be utilized. A large number of copolymers which can be formed by reacting various proportions of monomers from the aforesaid said list of polymers are also useful for preparing rate controlling structures useful in the invention.

While the non-rate controlling walls of the reservoir can be of any convenient thickness, usually they have a thickness of from 0.01 to 7 millimeters. The rate controlling membranes can have varying thickness depending upon the nature of the membrane, its porosity and the number of membranes used in combination. Typically, a thickness of from 20 to 200 microns is employed.

It will, of course, be appreciated that the pressure-sensitive adhesive surface need not form a continuous layer on the subject bandage. Particularly in the case of a bandage having a distinct reservoir layer, equally advantageous results are obtained by providing an annular surface of adhesive around the periphery of the bandage face. In this manner a liquid tight adhesive seal between the bandage and the patient's skin or mucosa is maintained, and at the same time, drug may be directly absorbed by the skin from the exposed surface of the drug reservoir layer without first migrating through an adhesive layer.

Any of the well known dermatologically acceptable pressure-sensitive adhesives can be used in practicing this invention. Exemplary adhesives include acrylic or methacrylic resins such as polymers of esters of acrylic or methacrylic acid with alcohols such as n-butanol, n-pentanol, isopentanol, 2-methyl butanol, 1-methyl butanol, 1-methyl penanol, 2-methyl penanol, 3-methyl pentanol, 2-ethyl butanol, isooctanol, n-decanol, or n-dodecanol, alone or copolymerized with ethylenically unsaturated monomers such as acrylic acid, methacrylic acid, acrylamide, methacrylamide, N-alkoxymethyl acrylamides, N-alkoxymethyl methacrylamides, N-tert-.butylacrylamide, itaconic acid, vinylacetate, N-branched alkyl maleamic acids wherein the alkyl group has 10 to 24 carbon atoms, glycol diacrylates, or mixtures of these; natural or synthetic rubbers such as styrenebutadiene, butylether, neoprene, polyisobutylene, polybutadiene, and polyisoprene; polyvinylacetate; ureaformaldehyde resins; phenolformaldehyde resins; resorcinol formaldehyde resins, cellulose derivatives such as ethyl cellulose, methyl cellulose, nitrocellulose, cellulose acetatebutyrate, and carboxymethyl cellulose; and natural gums such as guar, acacia, pectins, starch, dextrin, albumin, gelatin, casein, etc. The adhesives may be compounded with tackifiers and stabilizers as is well known in the art.

Various occlusive and non-occlusive, flexible or non-flexible backing members can be used in the adhesive patch of the invention. Suitable backings include cellophane, cellulose acetate, ethylcellulose, plasticized vinylacetate-vinylchloride copolymers, polyethylene terephthalate, nylon, polyethylene, polypropylene, polyvinylidenechloride, paper, cloth, and aluminum foil. Preferably, a flexible occlusive backing is employed to conform to the shape of the body member to which the adhesive tape is applied and to enhance administration of the agent to the skin.

To prevent passage of the drug away from the exposed surface of the pressure-sensitive adhesive prior to use, the adhesive surface of the tape generally is covered with a protective release film or foil such as waxed paper. Alternatively, the exposed rear surface of the backing member can be coated with a low-adhesion adhesive and the bandage rolled about itself. To enhance stability of the active compounds, the therapeutic bandage is usually hermetically sealed between appropriate layer such as polyethylene terephthalate films under an inert atmosphere, such as gaseous nitrogen.

To use the adhesive patch of the invention, wherein the drug is topical, it is applied directly to the area of skin to be treated, to release a therapeutically effective amount of the agent to the affected area. For administration of systemic drugs the bandage ca be applied to any area of the patient's skin, with the lower back, chest and buttocks being the areas of choice. In like manner, the patch can be applied to t he mucosa of the mouth, for example, by application to the palate or the buccal mucosa, to obtain absorption of the drug by the oral mucosa. Similarly, where desired and accessable, the patch can be applied to other mucosa membranes.

The following examples more specifically describe the invention; however, the scope of the invention is not limited to the embodiments set forth therein.

EXAMPLE 1

A transdermal system according to the invention is manufactured as follows:

A drug reservoir formulation is prepared by dispersing nitroglycerin 10% on lactose in silicon fluid containing colloidal silica as a suspension stabilizer, the final concentration of nitroglycerin in the formulation being adjusted to 5% w/w.

A silicon based contact adhesive solution in hexane is cast onto a 100 micron thick notched film of polyvinylchloride (PVC). After drying of the adhesive the adhesive side of this assembly is laminated to a 50 micron thick membrane of ethylene-vinyl acetate (EVA) copolymer leaving a strip at one side free of adhesive.

Figure 8:
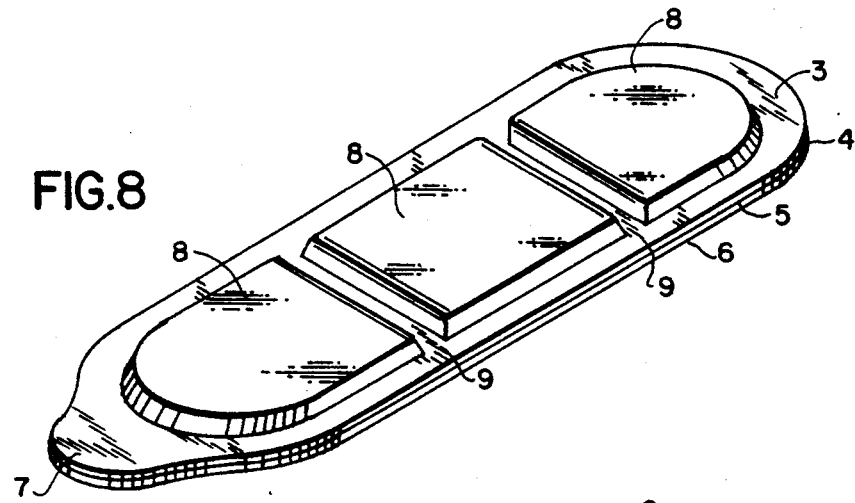

Three 1 g portions of the nitroglycerin suspension are placed beside each other on the EVA copolymer side of the described laminate and a 60 micron thick backing film of aluminized polyethylene terephthalate with an EVA heat sealable coating is laid over the portions of drug reservoir formulation and heat sealed at the periphery and between the individual portions as shown in FIG. 8.

Figure 9:
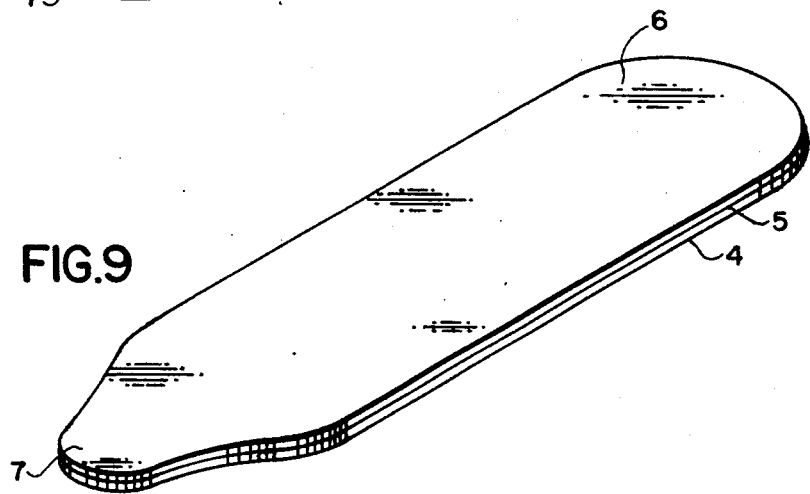
FIGS. 9-12 are various views of FIG. 8.
Figure 10:
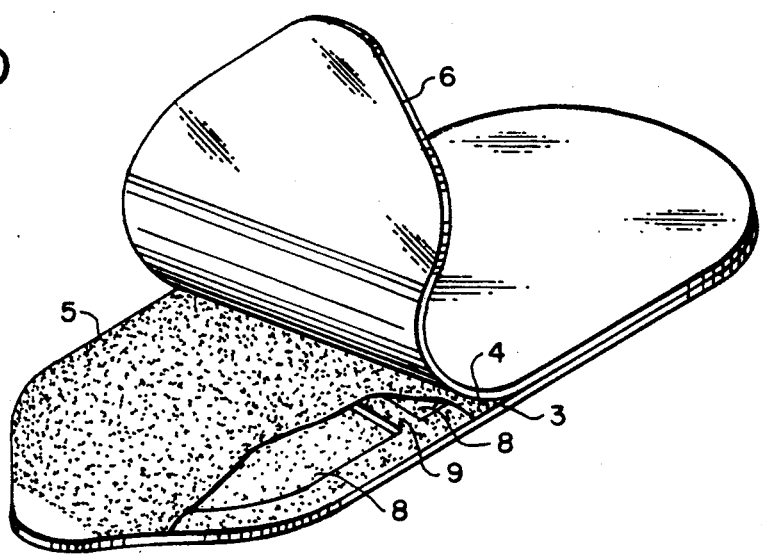
Figure 11:
Figure 12:
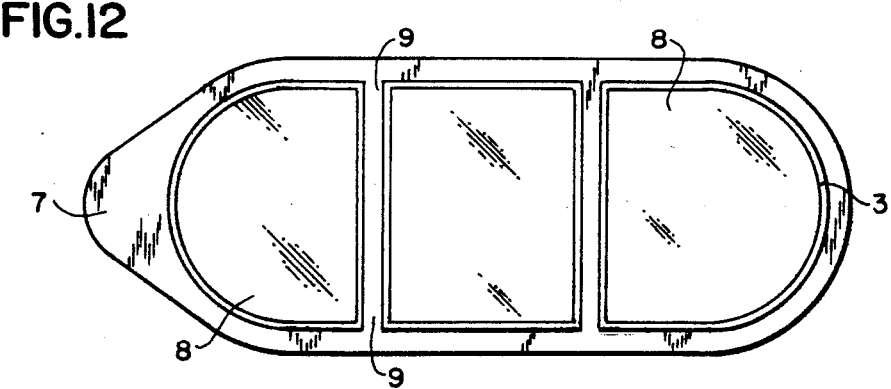
Figure 13:
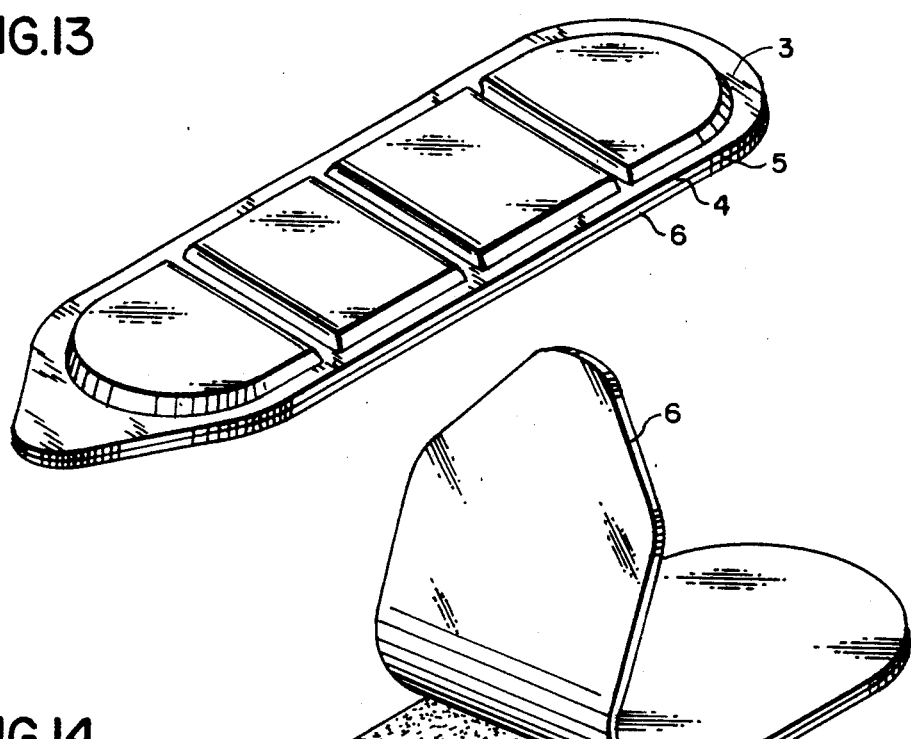
FIGS. 13, 14 and 15 are various views of a four compartment system analogous to FIGS. 8, 10 and 11.
Figure 14:
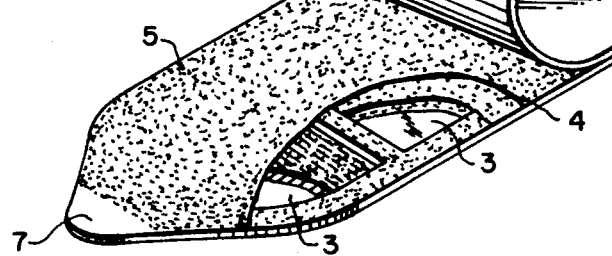
Figure 15:
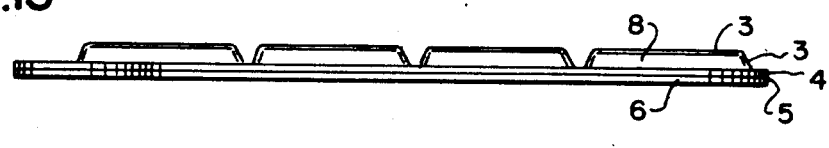
Figure 16:
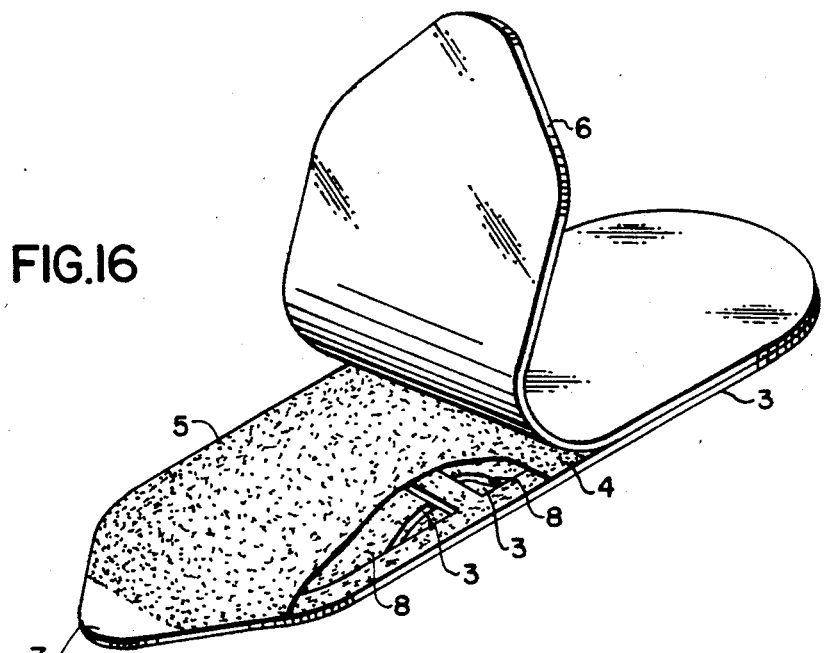
FIG. 16 is identical to FIG. 10 except that the compartments do not not contain the identical substance and/or concentration.

The finished system having 3 chambers with a contact area of 20 cm$^2$ for each of the 1 g reservoir portions is punched as shown in FIGS. 8, 9, and 11. FIG. 10 shows the opening tab on one side of the system which is left free of adhesive.

The system has an an active drug releasing surface of 60 cm$^2$ and delivers 30 mg of nitroglycerin within 24 hours through intact human skin in vivo.

What is claimed is:
1. In a transdermal or dermal patch for administering a controlled amount of a drug to skin or mucous membrane comprising, in sequence,
  A. a backing layer which is not permeable to said drug,
  B. a first membranous layer permeable to said drug, said first membranous layer and said backing layer being sealed together so as to define an enclosure for containing said drug,
  C. said drug contained within said enclosure,
  D. an adhesive layer on said first membranous layer, and
  E. a first removeable protective layer on said adhesive layer,
the improvement which comprises
  subdividing said enclosure into at least two compartments, at least one of said compartments containing therein a drug, drug concentration, or drug formulation which differs from that contained in at least one other of said compartments.

2. The patch of claim 1 wherein each compartment is no greater than 30 cm² in area.

3. The patch of claim 1 wherein the maximum distance from the center of gravity of a compartment and a boundary of said compartment is 2.70 cm.

4. The patch of claim 1 wherein the perimeter of a compartment is no greater than 4.04 times the square root of that compartment area.

5. In a transdermal or dermal patch for administering a controlled amount of a drug to skin or mucous membrane comprising, in sequence,
   A. a backing layer which is not permeable to said drug,
   B. a first membranous layer permeable to said drug, said first membranous layer and said backing layer being sealed together so as to define an enclosure for containing said drug,
   C. said drug contained within said enclosure,
   D. an adhesive layer on said first membranous layer, and
   E. a first removeable protective layer on said adhesive layer,
   the improvement which comprises
      subdividing said enclosure into at least two compartments, at least one of said compartments containing therein a drug, drug concentration, or drug formulation which is the same as or differs from that contained in at least one other of said compartments wherein at least one compartment, but not all, is modified by having a nonpermeable membrane thereon in addition to or in place of said first membranous layer or has an occlusive adhesive in addition to or in place of said adhesive layer so as to prevent said drug within said modified compartment from passing therethrough.

6. In a transdermal or dermal patch for administering a controlled amount of a drug to skin or mucous membrane comprising, in sequence,
   A. a backing layer which is not permeable to said drug,
   B. a first membranous layer permeable to said drug, said first membranous layer and said backing layer being sealed together to as to define an enclosure for containing said drug,
   C. said drug contained within said enclosure,
   D. an adhesive layer on said first membranous layer, and
   E. a first removeable protective layer on said adhesive layer,
   the improvement which comprises
      subdividing said enclosure into at least two compartments, at least one of said compartments containing therein a drug, drug concentration, or drug formulation which is the same as or differs from that contained in at least one other of said compartments wherein at least one compartment-compartment border comprises a non-burstable permeable membrane and a burstable, non-permeable membrane, said burstable membrane to be broken before, during, or after applying said patch to a patient.

7. In a transdermal or dermal patch for administering a controlled amount of a drug to skin or mucous membrane comprising, in sequence,
   A. a backing layer which is not permeable to said drug,
   B. a first membranous layer permeable to said drug said first membranous layer and said backing layer being sealed together to as to define an enclosure for containing said drug
   C. said drug contained within said enclosure,
   D. an adhesive layer on said first membranous layer, and
   E. a first removeable protective layer on said adhesive layer,
   the improvement which comprises
      subdividing said enclosure into at least two compartments, at least one of said compartments contained therein a drug, drug concentration, or drug formulation which is the same as or differs from that contained in at least one other of said compartments wherein a portion of said backing layer is replaced with a second permeable membrane in contact with said active agent, an additional adhesive layer on said second permeable membrane remote from said active agent and a second removeable protective layer on said additional adhesive, such that upon removal of said first removable protective layer, said patch may be folded upon itself, exposed adhesive to exposed adhesive to result in a final patch having one compartment located on top of another.

8. The patch of claim 1 wherein said drug is nitroglycerine or arecoline.

9. The patch of claim 1 wherein at least one compartment contains a drug formulation having a flux enhancer as a component thereof.

10. A method of administering a drug to a patient comprising removing said removeable layer from a patch of claim 1 to expose an adhesive layer and applying said patch absent said removeable layer, to said patient so that said adhesive layer contacts said patient.

11. The patch of claim 5 wherein said drug is nitroglycerine or arecoline.

12. The patch of claim 6 wherein said drug is nitroglycerine or arecoline.

13. The patch of claim 7 wherein said drug is nitroglycerine or arecoline.

14. The patch of claim 5 wherein at least one compartment contains a drug formulation having a flux enhancer as a component thereof.

15. the patch of claim 6 wherein at least one compartment contains a drug formulation having a flux enhancer as a component thereof.

16. The patch of claim 7 wherein at least one compartment contains a drug formulation having a flux enhancer as a component thereof.

17. A method of administering a drug to a patient comprising removing said removeable layer from a patch of claim 5 to expose an adhesive layer and applying said patch absent said removeable layer, to said patient so that said adhesive layer contacts said patient.

18. A method of administering a drug to a patient comprising removing said removeable layer from a patch of claim 6 to expose an adhesive layer and applying said patch absent said removeable layer, to said patient so that said adhesive layer contacts said patient.

19. A method of administering a drug to a patient comprising removing said second removeable layer from a patch of claim 7 to expose an adhesive layer and applying said patch absent said removeable layer, to said patient so that said adhesive layer contacts said patient.

* * * * *